United States Patent [19]

Schatz

[11] 3,942,016
[45] Mar. 2, 1976

[54] FILM CASSETTE
[75] Inventor: Joseph S. Schatz, Brooklyn, N.Y.
[73] Assignee: Wolf X-Ray Corporation, Jamaica, N.Y.
[22] Filed: June 29, 1971
[21] Appl. No.: 158,019

[52] U.S. Cl. .............. 250/475; 250/476; 250/480
[51] Int. Cl.² ........................................ G03B 41/16
[58] Field of Search ............ 250/67, 68, 69, 83 PH, 250/475, 476

[56] References Cited
UNITED STATES PATENTS

| | | | |
|---|---|---|---|
| 1,748,490 | 2/1930 | Martin | 250/67 |
| 2,213,437 | 9/1940 | Wolf | 250/68 |
| 2,562,453 | 7/1951 | Goldsmith | 250/67 |
| 2,812,441 | 11/1957 | Kamiss | 250/68 |
| 3,053,983 | 9/1962 | Faulkner, Jr. et al. | 250/83 |
| 3,296,437 | 1/1967 | Meschan | 250/67 |
| 3,482,097 | 12/1969 | Buck | 250/68 |

Primary Examiner—Craig E. Church
Attorney, Agent, or Firm—Lee C. Robinson, Jr.

[57] ABSTRACT

A cassette for holding radiographic film in which the edges of the cassette are provided with identifying indicia in accordance with a preselected code. The cassette includes a rectangular front panel facing one side of the film and a removable back panel facing the opposite side. This latter panel is provided with a lead coating and a layer of felt on the surface adjacent the film. The back panel serves as a cover for the cassette and is held in place by a pair of leaf springs which are supported for pivotal movement intermediate their ends. A hollow rectangular frame is disposed about the periphery of the panels, and each edge of the frame includes an indentation in close proximity with but spaced from one of the adjacent corners of the frame. Each of the indentations carries coded identifying indicia mounted entirely within the indentation.

7 Claims, 8 Drawing Figures

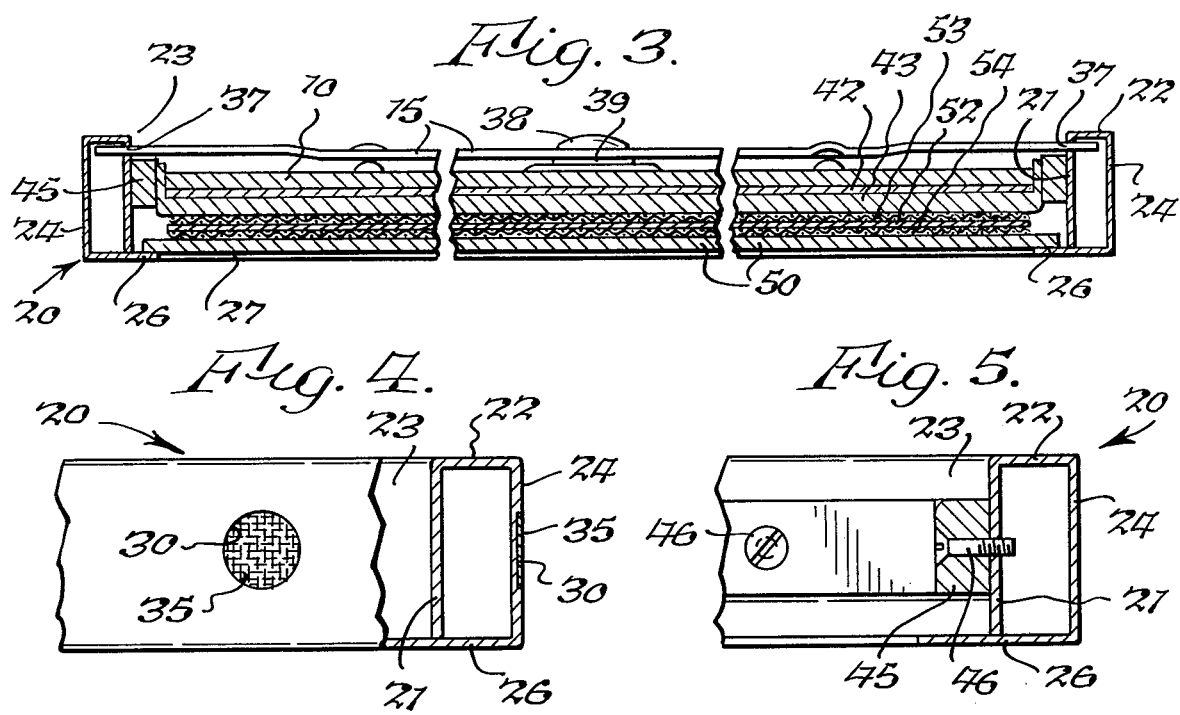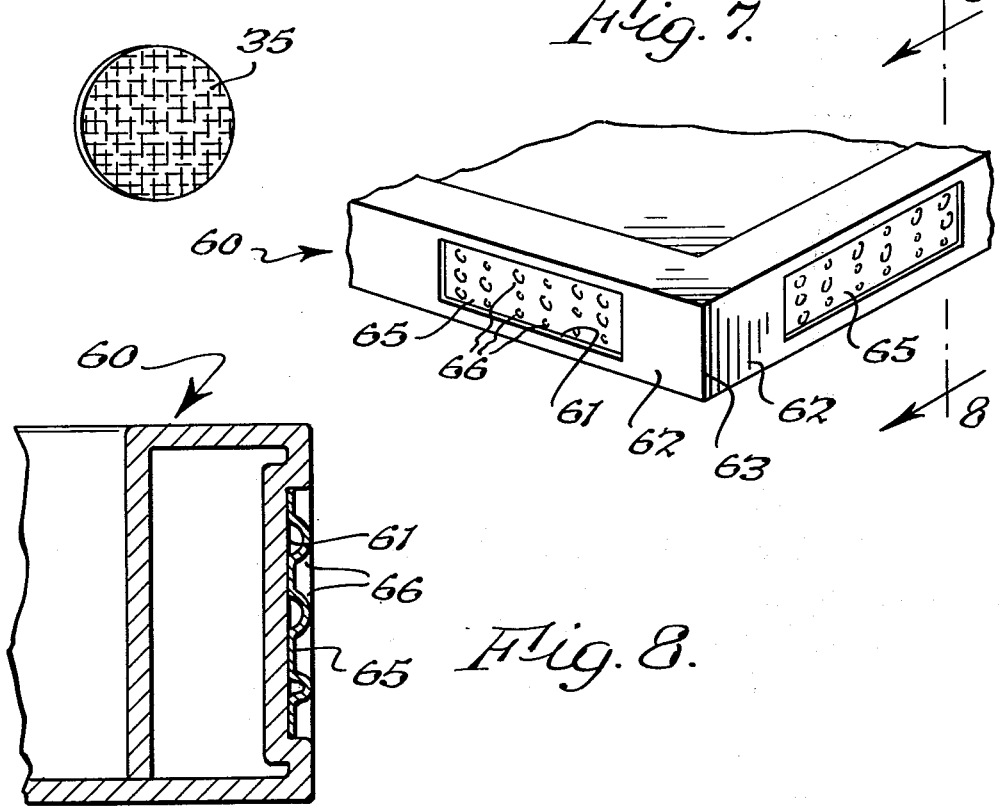

FILM CASSETTE

BACKGROUND OF THE INVENTION

This invention relates to film holding apparatus and more particularly to cassettes for holding radiographic film.

There has been developed a film cassette for x-ray or other radiographic film which is of unique, light-tight construction and is extremely simple to use. Representative cassettes of this type are disclosed in Harry S. Wolf U.S. Pat. No. 2,213,437 granted Sept. 3, 1940. Such cassettes customarily include a front panel and a back panel having a felt cushion. The film is positioned between intensifying screens located intermediate the two panels. The cassettes commonly are stored within the screens and film in place on shelves in radiographic rooms or other locations with only the edges of the cassettes visible. When a picture is to be taken, an orderly or technician selects the cassette with the appropriate screen and film combination, and the picture is made.

Heretofore, difficulties have been encountered in the construction and handling of film cassettes and similar film holding apparatus. Of particular importance is the need for rapidly and accurately identifying a given cassette and distinguishing it from the comparatively large number of adjacent cassettes at the storage location. In the making of an x-ray picture, for example, one of the more significant parameters is the speed of the screens within the cassette, and it is important to determine the screen speed quickly and without excessive handling. Also, information often is needed concerning the particular department or radiographic room in which the cassette has been stored, the type of cassette, e.g. photo-timing, grid cassette, etc., or other factors necessary or desirable to determine selected parameters consistent with the purpose for which the cassette is employed. Prior cassettes have proved deficient in these respects, with the result that in several instances the cassettes have been incorrectly identified and a substantial amount of time was wasted before the proper cassette could be located.

SUMMARY

One general object of this invention, therefore, is to provide a new and improved cassette or similar apparatus for holding radiographic film.

Another object of this invention is to provide such apparatus which may be readily identified merely by observing any one of the edges of the cassette.

A further object of the invention is to provide apparatus of the character indicated which is economical to manufacture and thoroughly reliable in operation.

In one illustrated embodiment of the invention, the apparatus includes a rectangular front panel for supporting radiographic film and a removable back panel overlying the film and having a planar surface in facing relationship therewith. The planar surface of the back panel is faced with lead and includes a layer of felted fibrous material between the lead and the film. The back panel is held in place by a pair of leaf springs which are supported for pivotal movement about axes intermediate the ends of the springs. The assembly of panels is surrounded by a rectangular frame member having four edge portions which meet at the four corners of the frame.

In accordance with one feature of the invention, the cassette includes an indentation which is arranged for the receipt of identifying indicia and is uniquely located on the cassette so that the indicia is readily accessible to the observer.

In accordance with another feature of the invention, in certain important embodiments, a plurality of indicia carrying indentations are provided at selected locations along the edge portions of the cassette. The arrangement is such that a hospital orderly or technician may readily select a particular cassette from the large number of cassettes commonly located in the cassette storage area.

In accordance with a further feature of several advantageous embodiments of the invention, each identifying indicia is mounted entirely within its identation. With this arrangement, the indicia cannot become caught on clothing, etc., during handling.

In accordance with a still further feature of the invention, in some arrangements, the indicia is arranged in accordance with Braille or other preselected code. As a result, a large number of screen speeds, cassette types, etc. may be readily identified in a rapid and straightforward manner.

The present invention, as well as further objects and features thereof, will be understood more clearly and fully from the following description of certain preferred embodiments, when read with reference to the accompanying drawings.

BRIEF DESCRIPTION OF THE DRAWINGS

FIG. 3 is a sectional view taken along the line 3—3 in FIG. 2.

FIG. 4 is an enlarged elevational view of a corner of the cassette, with certain portions shown broken away and in section.

FIG. 5 is an enlarged fragmentary sectional view similar to a portion of FIG. 3 but with certain parts omitted for purposes of clarity.

FIG. 6 is a perspective view of an identifying disk for the cassette.

FIG. 7 is a fragmentary perspective view of one corner of a cassette in accordance with another illustrative embodiment of the invention.

FIG. 8 is an enlarged fragmentary sectional view taken along the line 8—8 in FIG. 7.

DESCRIPTION OF CERTAIN PREFERRED EMBODIMENTS

Figure 1:
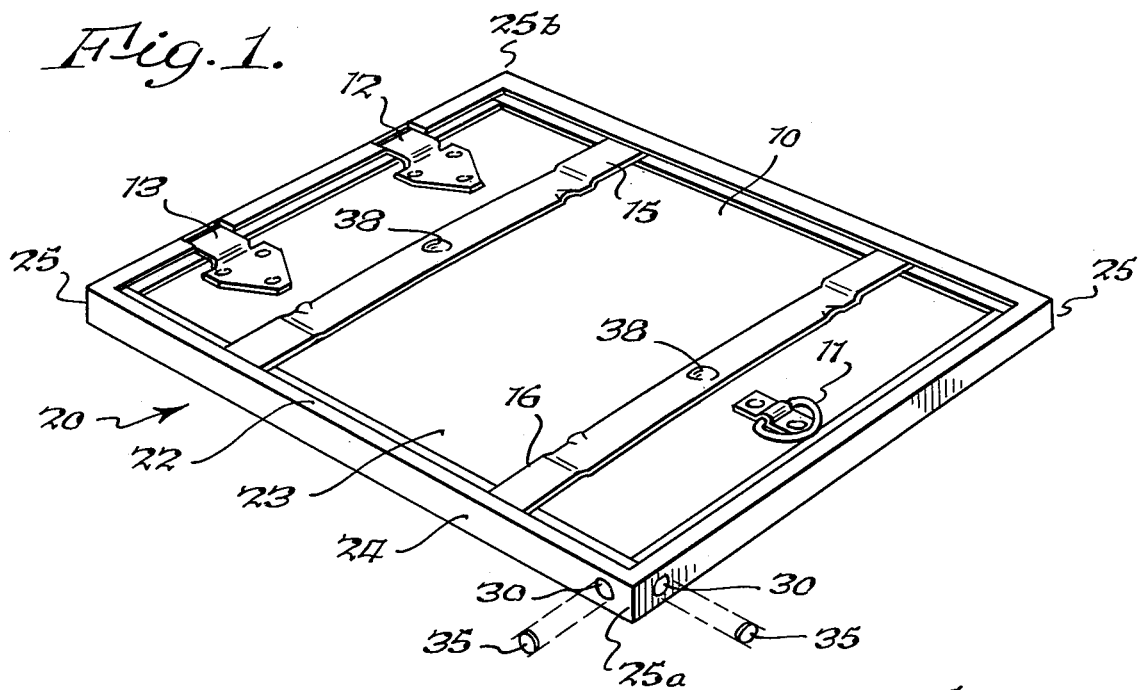
FIG. 1 is a perspective view of a cassette for holding x-ray film in accordance with one illustrative embodiment of the invention.
Figure 2:
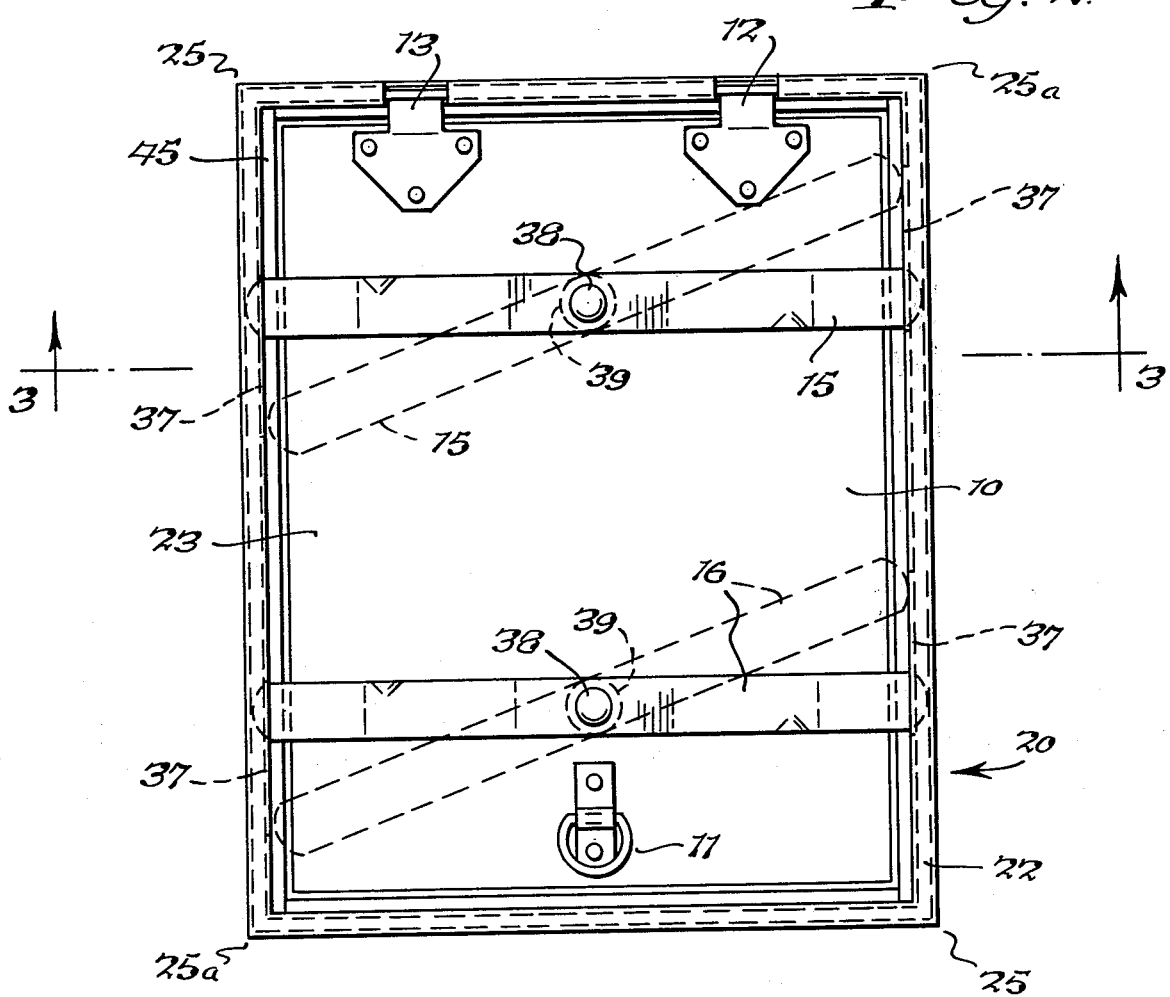
FIG. 2 is a plan view of the back of the cassette.

Referring to FIG. 1 and 2 of the drawings, there is shown a cassette for x-ray film which includes a rectangular cover panel 10. The panel 10 is provided with the usual D-shaped ring 11 for opening and closing the cassette and with two hinges 12 and 13 along the edge of the panel opposite that adjacent the ring 11. Two leaf springs 15 and 16 are pivotally supported on the panel 10 intermediate their ends for movement between the full line position shown in FIG. 2 and the dotted line position. These springs serve to hold the panel in place when the cassette is closed.

The hinges 12 and 13 are connected to one side of a hollow rectangular frame 20. As best shown in FIGS. 4 and 5, the frame 20 is of rectangular cross section, and each of the four sides of the frame is formed from a single sheet of stainless steel, for example. Each of the frame sides has an inner leg 21, a rear face portion 22 defining part of a back opening 23, an outer edge portion 22 defining part of a back opening 23, an outer edge portion 24 and a front face portion 26. The outer edge portions 24 extend in flat planes perpendicular to the plane of the cover panel 10 and meet at the four corners 25 of the frame. The front face portions 26 define a front opening 27 for the cassette which is smaller than the back opening 23.

A generally circular indentation 30 is provided in each of the edge portions 24 of the frame 20. The indentations 30 are arranged in pairs adjacent oppositely disposed corners 25a and 25b (FIGS. 1 and 2) of the frame. Each indentation is disposed in close proximity with but is spaced from the adjacent corner.

Identifying indicia in the form of a coded circular disk 35 is adhesively secured within each of the indentations 30. Each of the disks 35 is mounted entirely within its indentation such that the outer face of the disk is located either flush or inwardly with respect to the corresponding edge portion 24. In an illustrative example, the thickness of each edge portion 24 is .035 inches, the thickness of the disk is 0.010 inches and the depth of the indentation 30 is 0.012 inches. The disks may be fabricated from a suitable vinyl material and may include an adhesive coating on their inner faces.

The disks 35 are color coded in accordance with the desired identification of the cassette. Thus, each of the disks on a given cassette may be yellow, for example, to designate a particular screen speed, the cassette's storage location, the type of cassette, etc. Cassettes with different screen speeds, storage locations or characteristics may include disks of black, red, blue, green, gold, silver or other colors in accordance with a preselected code. The arrangement is such that, merely by observing the color of the disk on any one of the four edges of the cassette, a hospital orderly or technician can readily distinguish a particular cassette from adjacent cassettes.

As best shown in FIGS. 2 and 3, the inner legs 21 of the frame member 20 include slots 37 which accommodate the ends of the leaf springs 15 and 16. Each of the springs 15 and 16 is arranged for pivotal movement about the axis of a rivet 38 which extends through the midpoint of the spring and is affixed to the cover panel 10. A low friction bearing in the form of a nylon washer 39 is disposed between each spring and the cover panel and serves to provide extremely smooth and even movement of the spring between its open and closed positions.

The inner surface of the cover panel 10 is provided with a lead casing 42, and adhesively secured to the coating 42 is a layer of felted fibrous material 43. The edges of the felt 43 extend upwardly and engage a molding 45. This molding extends around the inner periphery of the frame 20 and is rigidly but releasably secured to the inner legs 21 of the frame by screws 46 (FIG. 4). The cover 10 may be quickly and easily lifted from its position adjacent the molding upon the release of the springs 15 and 16.

A rectangular front panel 50 rests on the inner surfaces of the frame face portions 26. The panel 50 illustratively is fabricated of magnesium or other x-rays translucent material but includes a front facing of Bakelite which is of the same color as the identifying disks 35. The dimensions of the panel 50 are larger than the dimensions of the front opening 27 but are smaller than the rectangle formed by the inner legs 21. With this arrangement the panel is positively held in place between the face portions 26 and the molding 45 but is free to expand and contract without affecting the dimensional stability of the frame.

To prepare the cassette for the taking of a radiograph, the appropriate radiographic film 52 is interposed between the usual intensifying screens 53 and 54, and the film and screens in position are supported by the inner surface of the front panel 50. The back or cover panel 10 is then located in overlying relationship with the film, with the felt 43 facing the uppermost screen 53. Upon the closing of the cover 10, the leaf springs 15 and 16 are pivoted from their dotted line position (FIG. 2) to their full line position, and the ends of the springs are located within the slots 37 in the frame member 20. The springs resiliently hold the cover in fixed relationship with the film 52.

Referring to FIGS. 7 and 8, there is shown an alternative coding arrangement for the identifying indicia on the cassette. The cassette of these figures include a frame 60 which is generally similar to the frame 20 described heretofore but is provided with somewhat larger, rectangular indentations 61 in the edge portions 62 of the frame. Like the indentations 30 of the previous embodiment, the indentations 61 are arranged in pairs adjacent oppositely disposed corners 63 of the frame.

Supported within each of the indentations 61 is a rectangular indicia bearing sheet 65. Each of the sheets 65 include a series of protuberances 66 arranged in Braille or other alpha-numeric code. The sheets 65 are adhesively mounted entirely within the corresponding indentations so that the protuberances 66 do not extend beyond the planes of the edge portions 62. The arrangement of the protuberances 66 on all of the sheets 65 for a given cassette is the same, and at least one of the sheets is located on each of the four edges of the cassette. As a result, the cassette may be quickly and easily identified and distinguished from adjacent cassettes merely by observing the pattern of the protuberances or by touching any one of the sheets. If desired, the sheets on respective cassettes may be of different colors to further facilitate their visual identification.

Although the invention has been described and illustrated as having particular utility in the identification of x-ray film cassettes, it also may be advantageously employed to identify other types of film holding equipment. As an illustration, the invention may be used by photographers, etc., for the identification of film packs and similar devices. Various other uses will suggest themselves to those skilled in the art upon a perusal of the foregoing disclosure.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

What is claimed is:

1. A light-opaque cassette for X-ray film comprising, in combination:

a rectangular front panel of X-ray transparent material for supporting X-ray film;

a removable back panel overlying the film and having a planar surface in facing relationship therewith;

means for holding the back panel in fixed relationship with the film;

a rectangular frame member disposed about the periphery of the panels, said frame member having face portions forming a back opening for receiving the back panel and a front opening for receiving the front panel and having inner and outer edge portions extending in planes perpendicular to said planar surface, the dimensions of said rectangular front panel being larger than the corresponding dimensions of said front opening but being smaller than the corresponding dimensions of the rectangle formed by said inner edge portions, the outer edge portions meeting at the corners of said frame member, each of said outer edge portions including an indentation in close proximity to but spaced from one of said corners; and identifying indicia means mounted within the indentation in each of the outer edge portions of said frame member such that one of the indicia means is visible upon viewing any one of said outer edge portions, the indicia means being rigidly affixed to said outer edge portion and serving to distinguish said cassette from similarly situated cassettes, the film within said cassettes being visually indistinguishable.

2. A cassette as defined in claim 1, in which said indentations are arranged in pairs adjacent oppositely disposed corners of said frame member.

3. A cassette as defined in claim 2, in which each of the identifying indicia means includes a series of raised protuberances.

4. A light-opaque cassette for radiographic film comprising, in combination:

a rectangular front panel for supporting radiographic film;

a removable back panel overlying the film and having a planar surface in facing relationship therewith, one of said panels being of radiation transparent material;

means defining a lead coating on said planar surface; a layer of felted fibrous material interposed between the coating and the film;

means for resiliently holding the back panel in fixed relationship with the film;

a hollow rectangular frame member disposed about the periphery of the panels, said frame member having face portions forming a back opening for receiving the back panel and a front opening for receiving the front panel and having inner and outer edge portions extending in planes perpendicular to said planar surface, the dimensions of said rectangular front panel being larger than the corresponding dimensions of said front opening but being smaller than the corresponding dimensions of the rectangle formed by said inner edge portions, each of the outer edge portions including an indentation therein, said indentations being arranged in pairs adjacent selected corners of said frame member; and identifying indicia means separate from said frame member and adhesively mounted within the indentation in each said outer edge portion such that one of the indicia means is visible upon viewing any one of said outer edge portions, the indicia means being rigidly affixed to said outer edge portion and serving to distinguish said cassette from similarly situated cassettes, the film within said cassettes being visually indistinguishable.

5. A light-opaque cassette for radiographic film comprising, in combination:

a rectangular front panel of X-ray transparent material for supporting radiographic film;

a removable back panel overlying the film and having a planar surface in facing relationship therewith;

means defining a lead coating on said planar surface;

a layer of felted fibrous material interposed between the coating and the film;

means for resiliently holding the back panel in fixed relationship with the film, the holding means including at least one leaf spring supported for pivotal movement about an axis intermediate the ends of the spring and low friction bearing means interposed between the leaf spring and the back panel;

a hollow rectangular frame member disposed about the periphery of the panels, said frame member having face portions forming a back opening for receiving the back panel and a front opening smaller than the back opening for receiving the front panel, the frame member having inner and outer edge portions extending in planes perpendicular to said planar surface, the dimensions of said rectangular front panel being larger than the corresponding dimensions of said front opening but being smaller than the corresponding dimensions of the rectangle formed by said inner edge portions, the outer edge portions meeting at the corners of said frame member, each of said outer edge portions including an indentation in close proximity to but spaced from one of said corners;

molding means rigidly but releasably attached to the inside periphery of said frame member for engaging the back panel when it is in said fixed relationship; and identifying indicia means mounted within the indentation in each of the outer edge portions of said frame member such that one of the indicia means is visible upon viewing any one of said outer edge portions and any one of said corners, the indicia means being rigidly affixed to said outer edge portion and serving to distinguish the particular type of cassette from similarly situated but different type cassettes, the film within said cassettes being visually indistinguishable.

6. A cassette as defined by claim 5, in which the low friction bearing means comprising a nylon washer.

7. A cassette as defined in claim 5, in which the identifying indicia means comprises a series of protuberances arranged in accordance with a predetermined code and located entirely within said indentations.

* * * * *